United States Patent
Janschitz et al.

(10) Patent No.: US 9,886,560 B2
(45) Date of Patent: Feb. 6, 2018

(54) PROCESS FOR THE MANAGEMENT OF DATA OF ANALYSIS DEVICES, ANALYSIS DEVICE AND SYSTEM COMPRISING ANALYSIS DEVICES

(75) Inventors: Wolfgang Janschitz, Graz (AT); Klaus Gromann, Graz (AT); Christian Kargl, Graz (AT)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 0 days.

(21) Appl. No.: 12/713,285

(22) Filed: Feb. 26, 2010

(65) Prior Publication Data

US 2011/0066805 A1      Mar. 17, 2011

Related U.S. Application Data

(63) Continuation of application No. PCT/EP2009/066774, filed on Dec. 9, 2009.

(60) Provisional application No. 61/121,945, filed on Dec. 12, 2008.

(51) Int. Cl.
*G06F 12/00*      (2006.01)
*G06F 19/00*      (2011.01)

(52) U.S. Cl.
CPC ............ *G06F 19/366* (2013.01); *G06F 12/00* (2013.01)

(58) Field of Classification Search
CPC .................................................... G06F 19/366
USPC ................ 711/103, 161, 162, 165; 705/2, 3; 707/640
See application file for complete search history.

(56) References Cited

U.S. PATENT DOCUMENTS

| | | | |
|---|---|---|---|
| 3,504,376 A | 3/1970 | Bednar et al. | |
| 4,043,756 A | 8/1977 | Sommervold | |
| 6,961,617 B1 | 11/2005 | Snell | |
| 7,964,147 B2 | 6/2011 | Schulat et al. | |
| 8,310,698 B2 | 11/2012 | Ogasawara et al. | |
| 9,377,452 B2 | 6/2016 | Bartel et al. | |
| 2001/0051952 A1 | 12/2001 | Nakazato | |
| 2002/0023198 A1* | 2/2002 | Kokubun et al. | ............. 711/162 |
| 2002/0023852 A1 | 2/2002 | McIvor et al. | |

(Continued)

FOREIGN PATENT DOCUMENTS

| | | |
|---|---|---|
| DE | 20113153 U1 | 3/2002 |
| EP | 1739538 A2 | 1/2007 |

(Continued)

OTHER PUBLICATIONS

Non-Final U.S. Office Action relating to U.S. Appl. No. 12/270,126 dated Apr. 9, 2010.

(Continued)

*Primary Examiner* — John A Lane
(74) *Attorney, Agent, or Firm* — Dinsmore & Shohl LLP

(57) ABSTRACT

A process for the management of data of an analysis device, which data serve for the operation of a further analysis device which is designed so as to be equivalent to the first analysis device, is disclosed. The analysis device newly creates or modifies data on an internal memory medium of the analysis device and the first analysis device, during its operation, continuously stores the newly created or modified data in a redundant manner in a non-volatile removable storage medium, with the removable storage medium being independent of the internal memory medium.

21 Claims, 4 Drawing Sheets

(56) References Cited

U.S. PATENT DOCUMENTS

| | | |
|---|---|---|
| 2003/0126494 A1* | 7/2003 | Strasser .................... 714/6 |
| 2005/0019213 A1 | 1/2005 | Kechagia et al. |
| 2005/0189219 A1 | 9/2005 | Amirkhanian et al. |
| 2005/0236273 A1 | 10/2005 | Han et al. |
| 2006/0041450 A1 | 2/2006 | Dugan |
| 2006/0148463 A1 | 7/2006 | Zhu et al. |
| 2006/0271607 A1 | 11/2006 | Yawata |
| 2006/0294420 A1 | 12/2006 | Schneider |
| 2007/0152683 A1 | 7/2007 | Werner et al. |
| 2007/0265884 A1 | 11/2007 | Lubell et al. |
| 2007/0271316 A1 | 11/2007 | Hollebeek |
| 2008/0015905 A1* | 1/2008 | Lubell et al. .................. 705/3 |
| 2008/0086609 A1* | 4/2008 | Lesser et al. .................. 711/162 |
| 2008/0099680 A1* | 5/2008 | Bauer et al. ............... 250/336.1 |
| 2008/0117447 A1 | 5/2008 | Okada et al. |
| 2008/0145277 A1 | 6/2008 | Wohland |
| 2008/0146922 A1* | 6/2008 | Steins et al. ................ 600/437 |
| 2008/0243959 A1* | 10/2008 | Bacastow et al. ............ 707/204 |
| 2008/0262776 A1 | 10/2008 | Yamasaki et al. |
| 2008/0309481 A1* | 12/2008 | Tanaka et al. ............ 340/539.12 |
| 2008/0312965 A1* | 12/2008 | Meshginpoosh ................ 705/3 |
| 2010/0037092 A1* | 2/2010 | Zamora ..................... 714/6 |

FOREIGN PATENT DOCUMENTS

| | | |
|---|---|---|
| JP | 2001-53913 A | 2/2001 |
| JP | 2002162213 A | 6/2002 |
| JP | 2003085423 A | 3/2003 |
| JP | 2005274469 A | 10/2005 |
| JP | 2007007873 A | 1/2007 |
| JP | 2008137372 A | 6/2008 |
| JP | 2008-200943 A | 9/2008 |
| JP | 2008-209328 A | 9/2008 |
| WO | 03/082091 A3 | 10/2003 |
| WO | 2004052195 A1 | 6/2004 |
| WO | 2005/040793 A1 | 5/2005 |
| WO | 2008134738 A1 | 11/2008 |

OTHER PUBLICATIONS

Final U.S. Office Action relating to U.S. Appl. No. 12/270,126 dated Nov. 29, 2010.

Non-Final U.S. Office Action relating to U.S. Appl. No. 12/270,126 dated Apr. 8, 2011.

Final U.S. Office Action relating to U.S. Appl. No. 12/270,126 dated Nov. 8, 2011.

Non-Final U.S. Office Action relating to U.S. Appl. No. 12/270,126 dated Mar. 16, 2012.

Non-Final U.S. Office Action relating to U.S. Appl. No. 12/270,126 dated Jul. 23, 2012.

Final U.S. Office Action relating to U.S. Appl. No. 12/270,126 dated Oct. 25, 2012.

Advisory Action relating to U.S. Appl. No. 12/270,126 dated Jan. 31, 2013.

Canadian Intellectual Property Office Examination Report dated Jul. 12, 2013 in reference to co-pending Canadian Patent Application No. 2,743,438.

Japanese Patent Office first Office Action dated Sep. 10, 2013 in reference to co-pending Japanese Patent Application No. 2011-540088.

Canadian Office Action dated Nov. 8, 2016, pertaining to Application No. 2,743,438 filed Dec. 9, 2009.

Japanese Office Action dated May 13, 2014 in related Japanese application No. 2011-540088 (English translation only), 4 pages total.

* cited by examiner

PROCESS FOR THE MANAGEMENT OF DATA OF ANALYSIS DEVICES, ANALYSIS DEVICE AND SYSTEM COMPRISING ANALYSIS DEVICES

CROSS REFERENCE TO RELATED APPLICATIONS

This application is a continuation of International Application No. PCT/EP2009/066774 filed Dec. 9, 2009, which claims priority to U.S. Provisional application Ser. No. 61/121,945 filed Dec. 12, 2008. This application is also related to U.S. patent application Ser. No. 12/633.892 filed Dec. 9, 2009, which also claims priority to U.S. Provisional application Ser. No. 61/121,945 filed Dec. 12, 2008.

TECHNICAL FIELD

Embodiments of the present invention relate to a process for the management of data of analysis devices, in particular for the transfer of data between a first and a second analysis device. Furthermore, certain embodiments of the invention relate to an analysis device and to a system comprising analysis devices. In addition, other embodiments of the invention relate to a computer program product by means of which the initially mentioned process is feasible on a programmable analysis device.

BACKGROUND

A typical area of application of such analysis devices or analyzers lies in the field of medicine/diagnostics where such devices are used, for example, for the analysis of body fluids, in particular for blood analysis.

Such analyzers are frequently used for the decentralized determination of point-of-care (POC) parameters, for example, of blood gases ($O_2$, $CO_2$, pH), electrolytes ($K^+$, $Na^+$, $Ca^{++}$, $Cl^-$), metabolites (glucose and lactate), haematocrit, haemoglobin parameters (tHb, $SO_2$, etc.) and bilirubin. In most cases, human whole blood serves here as a sample material, but applications in veterinary medicine and the use of serum, plasma, urine and dialysate samples are possible as well.

Such analyzers comprise appropriate measuring elements and arithmetic units associated therewith such as, e.g., programmable microcomputers or also application-specific circuits which control the functions of the analyzers and, accordingly, form a control stage. Furthermore, the analyzers comprise memory units (e.g., a 2.5" hard disk as a primary data storage device), which are also referred to as an internal memory medium. With the aid of those units, all settings (configuration data) as well as measuring results (measured data), user data and patient and subject data, respectively, (also those modifiable by a user) are usually stored internally. Possibly, some of these data can be exported upon request into other systems or onto other data storage devices and, respectively, can be imported from other systems or from other data storage devices. Standard protocols such as ASTM E 1394, 91 or POCT1-A or HL7 exist for data exchange with laboratory and hospital information systems or various server/client-based data and device management systems.

The problem of exchanging data in an electrochemical analysis device is also addressed in the German utility model specification DE 201 13 153 U1. In order to permit the exchange of data in an easy manner, a data reading and writing unit comprising an alternate semiconductor memory card is disclosed there as a solution. In the known case, the data reading and writing unit and the card replace an interface for the transmission of measured data and device parameters via a respective communication network to a central data processing station.

At this point, it should furthermore be mentioned that a process for backing up and restoring data in connection with a PC is disclosed in US 2006/0294420 A1. Such a data backup is usually executed in a time-controlled manner or is triggered manually. In this process, configuration data which are required for restoring the saved data are treated separately from the data to be saved in order to retrieve those configuration data more easily in case the data are restored.

Furthermore, at this point, US 2006/0148463 A1 should also be indicated in which the malfunction of a mobile phone is addressed, with the malfunction of the mobile phone having been caused mainly by incorrect or defective settings. In this context, their object is to restore original settings. Their object is achieved by a monitoring module which saves a plurality of original settings as soon as a SIM card is inserted in a mobile phone and restores the original settings if the settings of the mobile phone do not correspond to the original settings.

Neither the above-mentioned protocols nor the previously discussed disclosures in the patent and utility model literature solve the inherent problems of the data transfer in known analyzers. These data transfer methods, which have been used so far, exhibit in particular the following disadvantages:

- Manual interventions are necessary (e.g., selecting the data, starting the backup application).
- In case of necessity, a manual backup process normally implies a loss of data, since the data export is not performed immediately before the occurrence of an equipment failure.
- Possibly, separate coding and decoding of backup data is necessary.
- Solutions implemented in hardware (printer controller, disc controller, partially separate processors and interfaces to storage media) are normally expensive.

SUMMARY

It is therefore noted that the various embodiments of the present invention disclose a process, an analysis device, a system and a computer program product by means of which it is possible, especially in case of damage to an analysis device such as, e.g., to the control stage (arithmetic unit) or to the internal memory medium (data memory), to transfer all relevant data to a replacement analysis device in order to continue the analysis operation therewith as quickly and unproblematically as possible.

In accordance with one embodiment of the present invention, a process for the management of data of analysis devices, in particular for the transfer of data between a first and a second analysis device, is provided. The first analysis device newly creates or modifies data in an internal memory medium and, during operation, continuously stores the newly created or modified data in a redundant manner in a non-volatile removable storage medium. The data redundantly stored on the removable storage medium of the first analysis device are imported into the internal memory medium of a second analysis device.

In accordance with another embodiment of the present invention, an analysis device for the management of data for carrying out the above process is provided and comprises an internal memory medium for storing the data which are newly created or modified in the analysis device. The analysis device further comprises a memory interface for accessing a non-volatile removable storage medium so that, with the aid of the memory interface, the newly created or modified data can be continuously stored in a redundant manner in the removable storage medium during the operation of the analysis device.

In accordance with yet another embodiment of the present invention, a computer program product which is loadable directly into a main memory of a programmable analysis device is provided and comprises program code sections which implement the above process, if the computer program product is executed by means of the analysis device.

In accordance with still another embodiment of the present invention, a system comprising two analysis devices introduced above is provided, wherein data which are continuously newly created or modified in one of the two analysis devices during the operation of one analysis device, and data redundantly stored in the removable storage medium serve for the operation of the other analysis device, if the other analysis device accesses the removable storage medium.

BRIEF DESCRIPTION OF THE DRAWINGS

In the following, the invention is illustrated in further detail with reference to the attached figures, on the basis of an exemplary embodiment, to which the invention is not restricted, however. In the various figures, equal components are provided with identical reference numerals.

DETAILED DESCRIPTION

Figure 1:
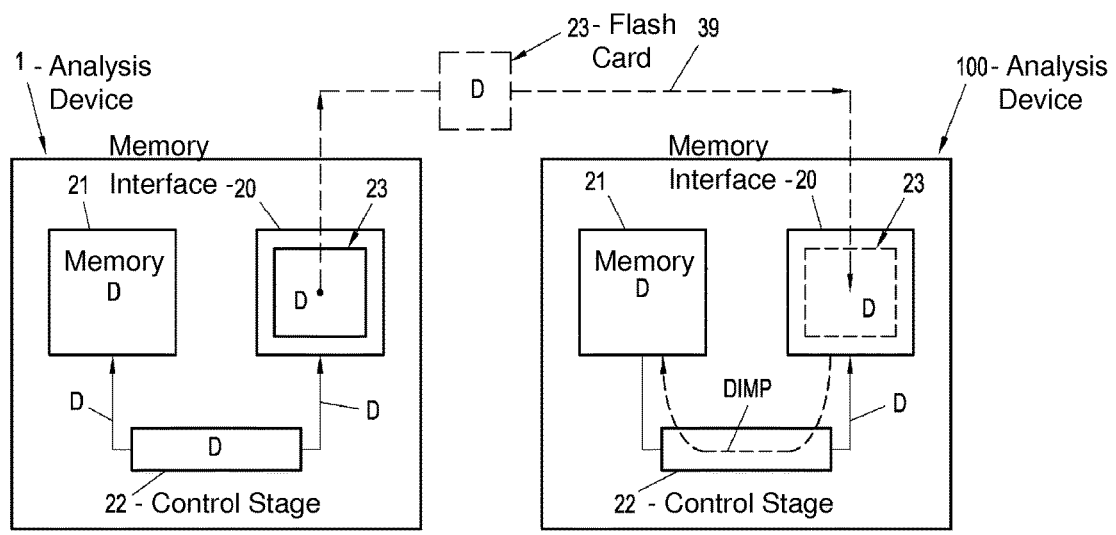
FIG. 1 shows an analysis device according to an exemplary embodiment of the invention in a strongly schematized manner and in the form of a block diagram.

In a process according to the invention for the management of data of analysis devices, in particular for the transfer of data between a first and a second analysis device, it is envisaged that the first analysis device newly creates or modifies data in an internal memory medium and, during operation, continuously stores the newly created or modified data in a redundant manner in a non-volatile removable storage medium and that the data redundantly stored on the removable storage medium of a first analysis device are imported into the internal memory medium of a second analysis device.

An analysis device according to the invention which manages data and is designed for carrying out the process according to the invention possesses an internal memory medium for storing the data which are newly created or modified in the analysis device and a memory interface for accessing a non-volatile removable storage medium so that, with the aid of the memory interface, the newly created or modified data are continuously storable in a redundant manner in the removable storage medium during the operation of the analysis device. The analysis device is a medical/diagnostic analysis device such as, e.g., an analysis device for the analysis of body fluids, in particular a blood analysis device.

The term "internal memory", as used herein, is understood to mean a volatile or non-volatile memory which must not be removed during the operation of the analysis device and is required for the operation of the analysis device. The internal memory may, for example, be designed as a semiconductor memory or a magnetic memory (hard disk) or an optical memory.

The removable storage medium is a non-volatile storage medium which is not required for the basic functionality of the analysis device, e.g., for performing analyses, but exclusively stores data present on the internal memory of the first analysis device in a redundant manner. The first analysis device does not use the data redundantly stored on the removable storage medium for its operation. In that sense, the removable storage medium is independent of the internal memory. However, as will be explained further below, it may be envisaged for safety reasons that the analysis device goes into or continues operation only if access to the removable storage medium is possible.

With a computer program product according to the invention, it is furthermore envisaged that the computer program product is loadable directly into a main memory of a programmable analysis device and comprises program code sections which implement the process according to the invention if the computer program product is executed by means of the analysis device.

By providing the measures according to the invention, it is advantageously achieved that the relevant data, in addition to being stored on a primary internal memory medium, are also continuously stored in a redundant manner on a second non-volatile removable storage medium during the operation of the analysis device, with the second storage medium not being integrated in the analysis device. Since the internal memory medium and the removable storage medium are independent of each other, i.e., no functional link exists between them, data errors which randomly occur on the internal memory medium when data are created and/or modified cannot propagate to the removable storage medium. According to the invention, it is envisaged that the analysis device, during its operation, continuously stores the newly created and/or modified data in a redundant manner in a non-volatile removable storage medium. This means that the data are redundantly written onto the additional removable storage medium immediately after their creation (e.g., in the internal memory medium or even directly in the control stage). No data mirroring is thereby performed, but the data are written independently of the other storage medium. This also constitutes a difference from a "Redundant Array of Independent Disks" (RAID) system. Namely, such a RAID system serves for arranging several physical hard disks of a computer into a logical drive which allows higher data integrity, should individual hard disks fail. Thus, e.g., in a combination of two hard disks which form the logical drive, the same data are mirrored onto all hard disks, i.e., are created redundantly. However, a mirror disk is no replacement for a data backup in the conventional sense, since inadvertent or defective writing operations also spread immediately to the mirror disks. In contrast and according to the invention, data are hence written independently of each other onto storage media which are independent of each other so that the problems inherent to the RAID system are avoided.

In a typical embodiment, the non-volatile second (external) storage medium, i.e., the removable storage medium, is a CompactFlash card. In principle, however, all kinds of external non-volatile storage media may be used according to the invention, e.g., other memory cards, USB sticks or also external hard disks. These may be inserted directly into appropriate slide-in modules of the analysis device or connected to the analysis device via appropriate ports/interfaces. Embodiments can also be implemented in which the non-volatile second (external) storage media are connected via a network to the analysis device or the analysis devices, such as, for example, if the external non-volatile storage media are designed as network storage devices or network hard disks. If both the first analysis device and a second analysis device are connected to the external non-volatile removable storage medium via a network, no physical transfer (change) of the external removable storage medium between the analysis devices is necessary. In fact, the data transfer can here occur by a respective access authorization of the equivalent second analysis device to the corresponding relevant redundant data of the first analysis device. Therefore, the designation "removable storage medium" has been chosen to indicate that, in contrast to the internal memory medium, the non-integrated (second) storage medium can be used alternately with respect to the two analysis devices.

In another typical embodiment of the invention, analysis devices are used for carrying out the process according to the invention which comprise appropriate slide-in modules (e.g., a CompactFlash card slot) or interfaces for connecting external non-volatile storage media and, furthermore, corresponding control elements (memory elements, writing elements, reading elements, data processing elements . . . ).

Thus, with the aid of the invention, it is advantageously achieved that the data can be transferred quickly and unproblematically to the second analysis device in case of malfunction or damage to the first analysis device. For the required data transfer from the first analysis device to the second analysis device, it is only necessary, for example, to remove the flash card from the first analysis device and insert it into the second analysis device. The data stored on the flash card are copied into the internal memory of the second analysis device. As a result, the second analysis device takes over all the stored data of the first analysis device which existed immediately before the abnormal occurrence. Subsequently, the flash card inserted into the second analysis device assumes the function of the redundant removable storage medium. The analyses performed, e.g., with the first analysis device can therefore be continued with the second analysis device actually without lengthy interruptions and practically seamlessly, whereby data consistency is preserved at the same time.

The area of application of the process lies in particular in the field of medical/diagnostic analysis devices, as is the case, e.g., with analysis devices for the analysis of body fluids, in particular blood analysis devices. In a typical embodiment, a first analysis device and the second analysis device equivalent thereto are formed by structurally identical analyzers in a system according to the invention.

In order to make sure that all necessary data exist for the operation of the equivalent analysis device, it has proved to be advantageous if—depending on the situation and the application—the data represent at least one of the data types indicated below or a plurality of the data types indicated below, namely:
  i) configuration data,
  ii) measured data,
  iii) subject data,
  iv) sample data, and
  v) user data.

Configuration data are understood to be in particular device settings such as language, IP address, display screen, country settings, energy management, network settings, calculated and displayed measuring units, measuring parameters used, measuring, calibration and quality control limits, quality measurement materials, security settings, audio settings, planned automatic executions of analyzer functions, peripheral devices etc.

Measured data comprise measuring results, raw data, image data, measuring signals, data which have been processed further, and the like.

Subject data comprise in particular patient identifiers.

Sample data comprise in particular sample identifiers, sampling time, sample type and/or sample taking temperature.

User data comprise in particular user identifiers, user-specific authorizations, user profiles and the like.

Since, in a typical embodiment, virtually all data types can also be written in redundantly, regular synchronization cycles between the storage media are not required. For calibration and quality control data which are purely device-specific (and hence should not readily be employed on the equivalent analysis device), the following possibilities exist:
  a) Calibration and quality control data which are purely device-specific are not written onto the removable storage medium (e.g., CompactFlash card).
  b) Calibration and quality control data which are purely device-specific are written also onto the removable storage medium (and a decision about their use is made only when the equivalent analysis device is put into operation).

The data integrity and the confidentiality of data, respectively, which typically are required for a medical data acquisition or another kind of data acquisition, can advantageously be obtained if at least the data stored in the removable storage medium are encoded. Furthermore, the data can be secured against misuse by passwords and/or user names. Thereby, the redundant data are optionally protected against unauthorized access.

In an embodiment of the process according to the invention, when the first analysis device is connected to a new removable storage medium, it will then export the data stored in the internal memory medium into the new removable storage medium, unless the storage medium already contains valid data of an external analysis device. Unintentional overwriting of valid data on the removable storage medium is thereby prevented.

In order to obtain a link between the analysis device and the removable storage medium, which is also referred to as a tuple, a unique identifier (e.g., serial number) of the removable storage medium, which is allocated to it, e.g., during the manufacture or delivery, may be stored in configuration data of the analysis device prior to the first startup (in the device-specific normal operation such as, e.g., in the measuring and/or analysis operation) of the analysis device. Alternatively, a unique identifier (e.g., serial number) of the analysis device, which is allocated to it, e.g., during the manufacture or delivery, may be stored on the removable storage medium prior to the first startup of the analysis device in order to produce an allocation of the data stored on the removable storage medium to the origin thereof, i.e., from which analysis device they originate.

For safety reasons, the existence of a uniquely identified external (removable) storage medium in the analysis device at the time of the system start and a validation thereof may optionally be required as a safety measure in order to allow the analysis device to go into operation. If the external storage medium is removed from the analysis device during running operation, this can be detected from an error occurring in the following write attempt. Thereupon, the analysis device can enter into a system stop state and be operated again only if the correct (removable) storage medium is present inside it. It is therefore advantageous if the availability of the removable storage medium is checked especially during a first startup of the analysis device and, if the removable storage medium is not available, the operation is not permitted at all or only to a limited extent, in particular, however, without redundant storage of relevant data on the removable storage medium.

In order to ensure that an analysis device cannot be put into operation with any removable storage medium for the purpose of the redundant storage of data, a reliable measure has turned out to be that the removable storage medium comprises a hardware token which is necessary for the operation of the analysis device.

If it is found that the removable storage medium is available, it is checked whether a data stock present on the removable storage medium originates from a different analysis device and, if this applies, those redundantly stored data contained in the removable storage medium are imported into the internal memory medium of the analysis device.

For safety reasons, the decision whether data redundantly stored in the removable storage medium are imported into the analysis device can be made dependent also on a user interaction. In case it is found that the removable storage medium is empty, the user interaction can be replaced by an automatic decision, namely to export data from the analysis device onto the removable storage medium. With regard to the import process, it is advantageous for the replicability of the data import if those processes are recorded, which may typically be carried out by means of a so-called audit trail.

According to a typical exemplary embodiment, the process according to the invention is implemented by means of an analysis device according to the invention which is programmable. The analysis device usually comprises a program memory, a main memory and a microprocessor, with the microprocessor forming a control stage of the analysis device and being coupled to the internal memory and the memory interface. By means of the program memory, a computer program is stored which implements the process according to the invention if it is executed by the microprocessor. However, the process may also be implemented by means of an analysis device in which an application-specific (e.g., hardwired) circuit is used the logic of which represents the process according to the invention.

Furthermore, a system comprising two analysis devices according to the invention is provided, wherein data which are continuously newly created and/or modified in one of the two analysis devices during the operation of one analysis device and data redundantly stored in the removable storage medium serve for the operation of the other analysis device, if the other analysis device accesses the removable storage medium.

Figure 3:
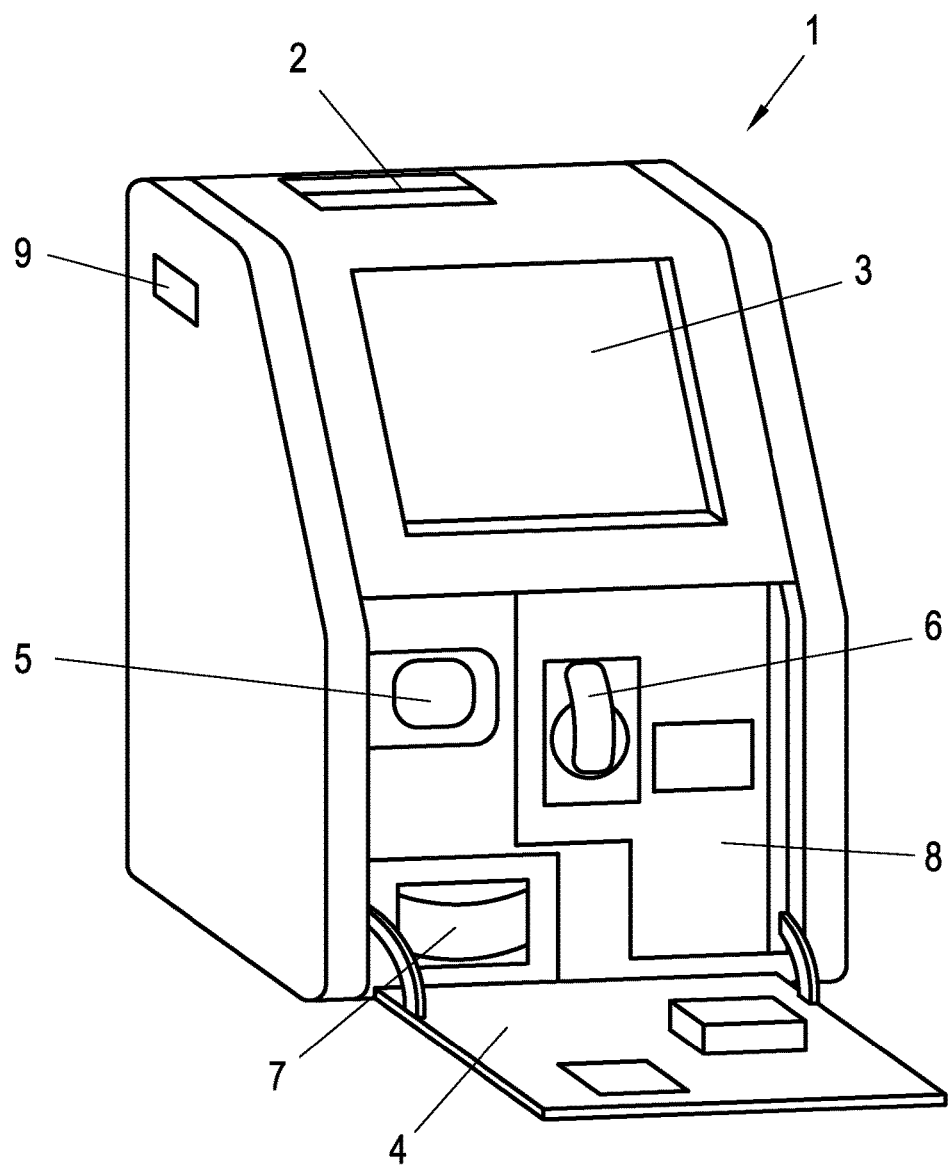
FIG. 3 shows, in a strongly schematized manner, the analysis device in a first perspective.
Figure 4:
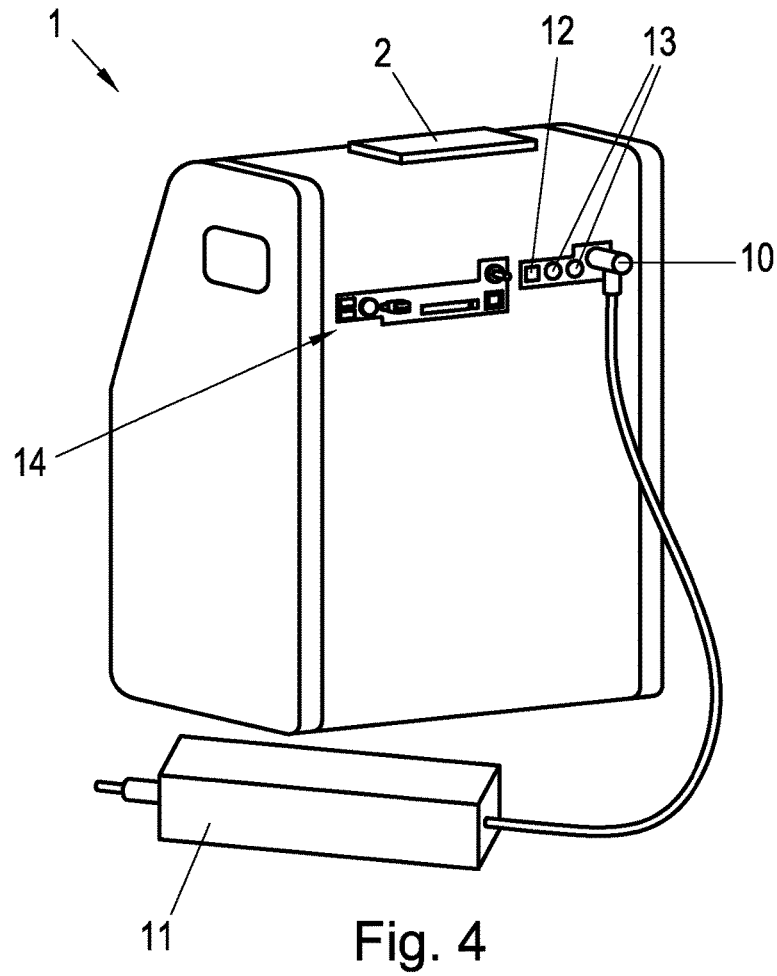
FIG. 4 shows the analysis device according to FIG. 3 in a second perspective.

FIGS. 3 and 4 show a possible construction and the components of a medical blood gas analyzer which are visible from outside, which blood gas analyzer implements the analysis device 1. In FIG. 3, the analysis device 1 is illustrated essentially from the front. A printer 2 forming part of a user interface is located on the top side of the analysis device 1. A screen 3, preferably a touch screen, which is arranged essentially on the front side of the analysis device 1, is likewise part of the user interface. An appliance door 4, which is illustrated in the opened state, is also located on the front side. The opened appliance door 4 gives a view over a measuring module 5 comprising a sensor cartridge, a sample-input module 6, an AutoQC module 7 and a fluid pack 8. A USB interface 9 is located on the right hand side of the analysis device 1. In FIG. 4, the analysis device 1 is illustrated essentially from the back. A mains connection 10 to which a power supply unit 11 is connected is located on the back side. By means of a power switch 12, the analysis device can be switched on and off. Two fuses and two status LEDs, which are summarized under reference numeral 13, are located between the power switch 12 and the mains connection 10. In addition, an interface area 14 is illustrated, which is addressed in detail in FIG. 5.

Figure 5:
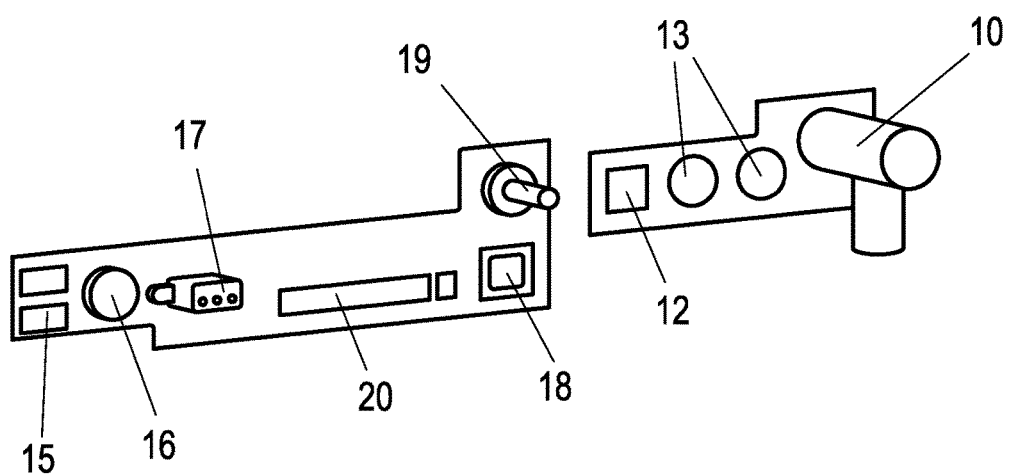
FIG. 5 shows a detail of the analysis device according to FIG. 3.

The interface area illustrated in FIG. 5 comprises two USB connections 15, a connection for a barcode scanner 16, an RS 232 service plug 17, an RJ 45 network connection 18, a potential equalization plug 19 and a memory interface 20 for a flash card. In the following, the function of the memory interface 20 is addressed in further detail with reference to FIG. 1 and FIG. 2.

In FIG. 1, a block diagram of the analysis device 1 and of an analysis device 100 equivalent thereto is illustrated with the structural elements necessary for discussing the invention forming the subject manner. In the present case, the equivalent analysis device 100 is designed so as to be structurally identical to analysis device 1, which, however, is not mandatory. Besides the memory interface 20, the analysis device 1 comprises an internal memory medium 21 and a control stage 22. The coupling of the memory interface 20 and of the internal memory medium 21 to the control stage 22, which is sufficiently known to a person skilled in the art, is not addressed further at this point. In contrast to the equivalent analysis device 100, a flash card 23 is inserted in the analysis device 1 so that the data D newly created and/or modified in the internal memory medium 21 can be redundantly recorded also in the flash card 23. With the aid of the analysis devices 1 and 100, respectively, the process according to the invention can now be carried out, which will be explained below on the basis of FIG. 2.

Figure 2:
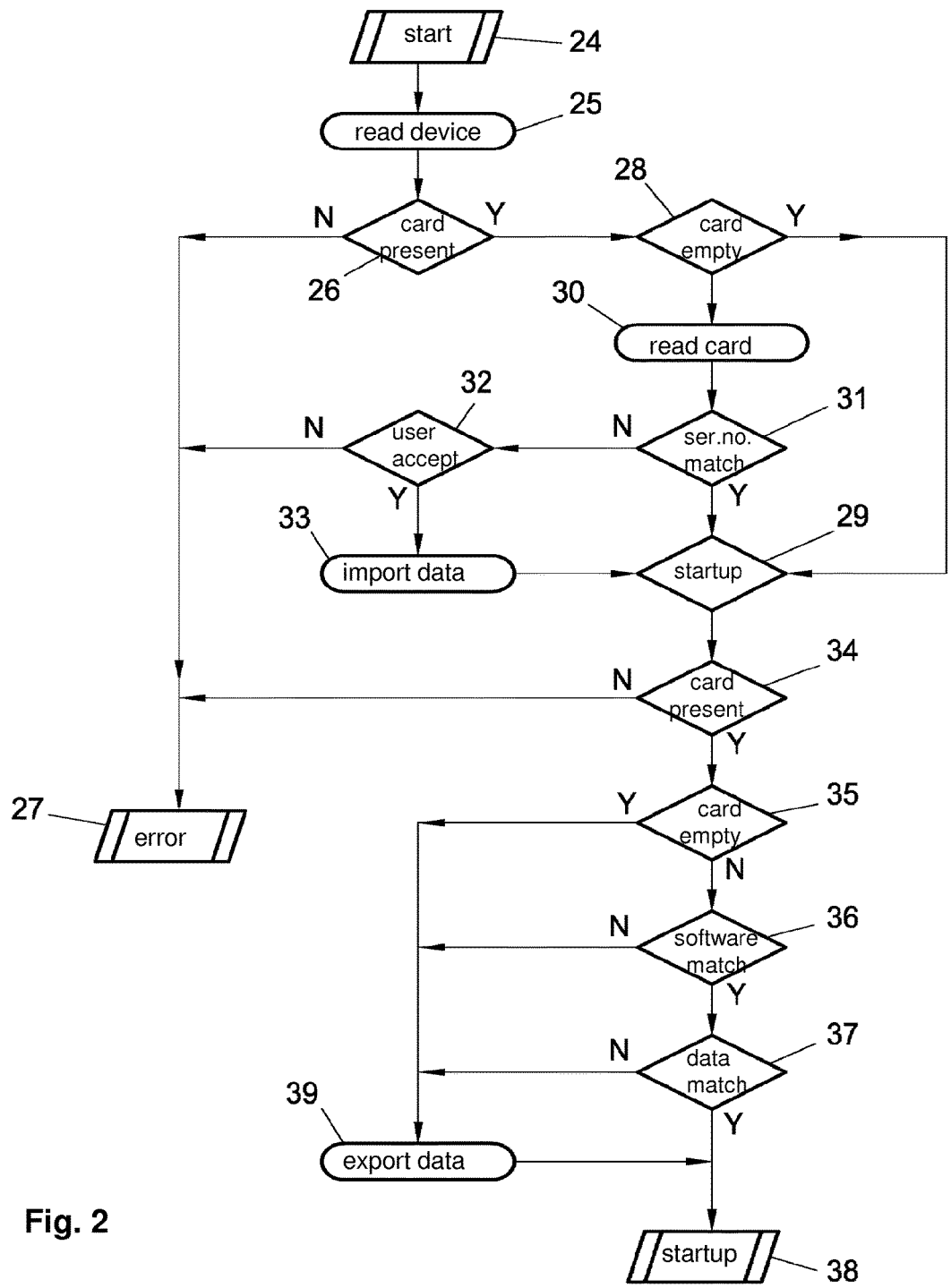
FIG. 2 shows a process according to the invention in the form of a flow diagram.

The beginning of the process illustrated in FIG. 2 is characterized by a block 24. In a subsequent block 25, the configuration of the analysis device 1 is read. This is followed by a branch to a block 26 in which it is checked whether a flash card 23 is available in the memory interface 20. If this is not the case, the operation of the analysis device 1 is stopped in block 27 with an error message. Alternatively, a limited operation of the analysis device 1 could be allowed until a flash card 23 is eventually inserted.

In case of analysis device 1, the result of this check is positive and the process is continued in a block 28 in which it is checked whether the flash card 23 is empty. If the flash card 23 is empty, the further execution of the starting procedure is continued in a block 29. If the flash card 23 is not empty, the configuration of the flash card 23 is read in a block 30 and subsequently it is checked in a block 31 whether the serial number of the inserted flash card 23, which is contained in the configuration of the flash card 23, has remained the same as with the last startup of the analysis device 1. Alternatively, it can be checked here whether the serial number or a different identifier of the analysis device 1 corresponds to a serial number or identifier of an analysis device which is stored on the flash card 23.

If the serial number of the inserted flash card 23 is identical to the serial number of a flash card 23 stored in the internal memory of the analysis device (or alternatively, the serial number of the analysis device 1 stored on the flash card 23 is identical to the serial number of the currently used analysis device), which means that the flash card 23 continues to be located in the previously used analysis device 1, the starting procedure is continued in block 29. If the serial number of the inserted flash card 23 (or alternatively, the serial number of the analysis device 1 stored on the flash card 23) and hence also the previous allocation of flash card 23 and analysis device 1 have changed, a branch goes to a block 32 which represents a user interaction in which the user can agree to or reject an import of the data stored on the flash card 23 into the internal memory medium of the analysis device 1. If the user rejects this, the operation of the analysis device 1 is stopped in block 27 with an error message. If the user agrees to the import of data, the data import into the internal memory medium of the analysis device 1 is carried out in block 33, whereby a current allocation of removable storage medium and analysis device occurs via appropriate storing of identifiers of the removable storage medium or analysis device, and the starting procedure is continued in block 29. The user interaction 32 constitutes an additional safety feature, which optionally can also be omitted.

Block 29 marks the transition from a basic initialization of the analysis device 1 of the actual startup procedure to an onset of data logging, wherein, in a block 34, the presence of the flash card 23 in the analysis device 1 is again queried and, if the flash card 23 is not present, the operation of the analysis device 1 is stopped in block 27 with an error message.

If the flash card 23 is present, it is again checked in a block 35 whether the flash card 23 is empty. If the flash card 23 is empty, the data D stored, newly filed and/or modified in the internal memory medium of the analysis device 1 are exported in block 39 into the flash card 23 and subsequently, in block 38, the further startup of the analysis device is continued, which, however, is no longer of importance for the purposes of the present invention.

If the flash card 23 is not empty, it is checked in a block 36 whether the software version of the flash card 23 corresponds to that of the analysis device 1, i.e., whether the data present on the flash card 23 exist in the same structure as in the analysis device 1. If this does not apply, a branch goes to block 39 in which the data stored in the internal memory medium of the analysis device 1 are exported into the flash card 23; subsequently, the further startup of the analysis device is continued in block 38.

If the software version of the flash card 23 corresponds to that of the analysis device 1, it is checked in a block 37 whether the database of the flash card 23 corresponds to that of the internal memory medium 21 of the analysis device 1, i.e., whether the data present on the flash card 23 correspond to the data present in the analysis device 1. If the databases do not match, a branch goes to block 39 in which the data stored in the internal memory medium of the analysis device 1 are exported into the flash card 23; subsequently, the further startup of the analysis device is continued in block 38. If the databases match, a branch immediately goes to block 38.

Upon completion of the startup, the analysis device 1 enters into an operating mode in which newly created and/or modified data D are continuously stored in a redundant manner on the flash card 23. Thus, all data D to be transferred in the case of an error (e.g., configuration data, user data, patient data and measuring results) are written during the running operation of the analysis device 1 redundantly onto an additional removable storage medium, such as, for example, flash card 23 immediately after their formation. This corresponds to a normal operation (measuring or analysis operation) of the properly functioning analysis device 1.

If a flash card 23 is now inserted into the memory interface 20 of the equivalent analysis device 100, which flash card 23 was previously used on the analysis device 1 and was inserted into the new analysis device 100, for example, because problems had occurred in the previously used analysis device 1, the process is schematically illustrated by means of the broken line 39 in FIG. 1 and symbolizes the removal of the flash card 23 from the analysis device 1 and the insertion of the flash card 23 into the analysis device 100. Subsequently, the above-described startup procedures are run in the analysis device 100. The import of the data D present on the flash card 23 into the internal memory medium 21 of the analysis device 100 is indicated by the broken line characterized by reference sign DIMP. Thereupon, the normal operation of the equivalent analysis device 100 takes place.

In the further description of the process, it is assumed that the analysis device 1 was put into operation for the first time already in the past. The state is represented, for example, by corresponding data D in the internal memory medium 21.

At this point, it should optionally be mentioned that the user or also the analysis device 1 or 100, respectively, or also the flash card 23 itself can prevent the data D from being overwritten both on the internal memory medium 21 and on the flash card 23, which, however, is not illustrated in detail in FIG. 2.

The previously described analysis device 1 and 100, respectively, and the process feasible therewith now allow handling of various cases of damage. In damage case I (defective analysis device 1) and/or damage case II (defective PC) and/or damage case III (defective primary data carrier, i.e., internal memory medium 21), the external removable storage medium (e.g., flash card 23) is transferred to a standby analyzer (e.g., equivalent analysis device 100) and is installed and used further there.

As discussed before, the standby unit (a second analyzer, e.g., equivalent analysis device 100) may be a) a device which has never been put into operation (and hence does not contain such relevant data D), or also b) a device which was previously already put into operation (and hence already exhibits relevant data D based on the previous operation of the device). In both cases, the process according to the invention provides for procedural steps which meet the requirements of the respective case.

In damage case IV (defective external data carrier, i.e., removable storage medium 23), this can be renewed (replaced), with the relevant data D still being stored on the internal memory medium 21.

The following procedure may, for example, be taken for the commissioning of an analysis device 1:
  a) When the analyzer software is booted for the first time, the existence of a flash card 23 (designed, e.g., as a CompactFlash card) is checked. If no CompactFlash (CF) card 23 is present, the analysis device 1 cannot be started and operated, respectively. If, however, a flash card 23 is present, its serial number is read out. If the serial number does not correspond to the serial number filed in the configuration, the data D filed in the flash card 23 are imported into the database in the internal memory medium 21 of the analysis device 1. All changes are recorded in an audit trail.
  b) When the analyzer software is booted for the first time, the existence of a CompactFlash card 23 is checked. If no CF card 23 is present, an alert message which is displayed shows that the backup mode is not active and data D are not stored redundantly. Then, the backup mode may again be activated, e.g., manually or also automatically as soon as an empty CF card 23 is detected in the analysis device 1.

The following procedure may, for example, be taken for the exchange of the external removable storage medium 23:

a) If a flash card 23 which does not correspond to the flash card having a serial number stored in the configuration is detected on an analysis device which has already been put into operation, the relevant data D, in particular the configuration, user and measured data, are automatically exported from the database of the internal memory medium 21 onto the new card 23. The entire data D to be saved are written onto the new functional flash card 23.

b) If a flash card 23 which does not correspond to the flash card having a serial number stored in the configuration is detected on an analysis device 1 or 100, respectively, which has already been put into operation, and if the CF card 23 is not empty, a user may choose as to whether data D should be imported or exported.

Thus, with the aid of the invention, a process for the management and transfer of relevant data D of analysis devices 1 and 100, respectively, can also be described, wherein the analysis devices 1 and 100, respectively, each possess an internal memory medium 21 and the relevant data D refer to the specific configuration of a first analysis device 1 as well as to the parameter values, which so far have been measured with the first analysis device 1, and to the associated background information, comprising the steps of:

providing an additional external non-volatile storage medium 23 in the first analysis device 1, continuously storing all newly created and/or modified relevant data D in a redundant manner on the external non-volatile storage medium 23 and the internal memory medium 21 of the first analysis device 1 during the operation (analysis and measurement, respectively) of the first analysis device 1, in case the redundantly stored data D are transferred to a second analysis device 100, removing the external non-volatile storage medium 23 from the first analysis device 1 and inserting the external non-volatile storage medium 23 into the second analysis device 100, reading the relevant data D stored on the external non-volatile storage medium 23, which data were stored during the operation in the first analysis device 1, into the internal memory medium 21 of the second analysis device 100, continuing the operation (analysis and measurement, respectively) with the second analysis device 100, using those relevant data D which have been read in.

The advantages of the solution which have thus been obtained can be listed as follows:

By continuously storing all relevant data D in a redundant manner, no logic or temporal control of automatic synchronization cycles is necessary unlike in known backup processes.

The data stock can be reconstructed at any time, optionally at a point in time immediately before the abnormal occurrence (no quantization losses due to manual or automatic synchronization cycles).

By checking the existence of a uniquely identified external storage medium 23 and its use as a token, it is prevented that an analysis device 1 or 100, respectively, which can store data D only incompletely or not redundantly at all is put into operation.

By requiring the existence of a particular unique storage medium 23 during the commissioning and the implemented control, under which conditions an import scenario or an export scenario is provided, the necessity of a manual interaction is avoided.

An identical configuration can easily be transferred to many analysis devices 1 and 100, respectively.

In case of an abnormal occurrence, the recording of the above-mentioned data D may serve as a documentation and/or a bug report.

A user can immediately continue the measurement with his or her specific and familiar user interface on the second analysis device 100 without having to perform manual resettings on the standby unit 100.

Even if the invention was discussed within the context of a blood analyzer by reference to the description of the figures, the invention may also be used in other scientific and/or industrial applications. For the sake of completeness, it is also pointed out that the use of the indefinite articles "a" and "an", respectively, does not rule out that the respective features can be present also several times. Similarly, the terms "stage", "unit", "module" or "device" etc. do not rule out that they are made up of several components, which, optionally, may also be distributed spatially.

What is claimed is:

1. A process for the transfer of data between a first and a second analysis device, the process comprising:

newly creating or modifying data in an internal memory medium of a first analysis device, and continuously and automatically storing the newly created or modified data in a redundant manner in a non-volatile removable storage medium during at least body fluid analysis operations without synchronization of data stored in the internal memory medium of the first analysis device;

importing the data redundantly stored on the non-volatile removable storage medium of the first analysis device into internal memory medium of a second analysis device, wherein:

the first and second analysis devices are medical/diagnostic devices configured to receive as input and analyze body fluids, the second analysis device is an equivalent device to the first analysis device, the non-volatile removable storage medium is either directly inserted in a slide-in-module of the first analysis device or connected to the first analysis device, the data redundantly stored on the non-volatile removable storage medium are imported into the internal memory medium of the second analysis device by physically transferring the non-volatile removable storage medium between the first and second analysis devices, the data redundantly stored on the non-volatile removable storage medium is at least configuration data of the first analysis device, and the configuration data represents device settings that comprise language, IP address, display screen, country settings, energy management, network settings, calculated and displayed measuring units, measuring parameters used, measuring, calibration and quality control limits, quality measurement materials, security settings, audio settings, and/or planned automatic executions of analyzer functions and/or peripheral devices; and subsequent to physically transferring the non-volatile removable storage medium between the first and second analysis devices, both configuring automatically the second analysis device to have the identical configuration to the first analysis device based on the imported data via a startup process and continuing automatically with at least the body fluid analysis operations previously conducted by the first analysis device on the second analysis device based on the imported data.

2. The process according to claim 1, wherein the body fluid is blood.

3. The process according to claim 1, wherein the process further comprises redundantly storing in the removable storage medium data that represents at least one of the data types indicated below:
   i) measured data that comprises measuring results, raw data, image data, measuring signals and/or data which have been processed further,
   ii) subject data,
   iii) sample data that comprises sample identifiers, sampling time, sample type and/or sample taking temperature, and
   iv) user data that comprises user identifiers, user-specific authorizations and/or user profiles.

4. The process according to claim 1, wherein the data redundantly stored in the removable storage medium is encoded.

5. The process according to claim 4, wherein the encoded data is secured against misuse by passwords and/or user names.

6. The process according to claim 1, wherein the process further comprises connecting a new removable storage medium to the first analysis device such that the first analysis device exports the data stored in the internal memory medium into the new removable storage medium, unless said storage medium already contains valid data of an external analysis device.

7. The process according to claim 1, wherein the process further comprises, prior to a first startup of the first analysis device, storing a unique identifier of the removable storage medium in the internal memory medium the first analysis device or storing a unique identifier of the first analysis device in the removable storage medium.

8. The process according to claim 1, wherein the process further comprises checking the availability of the removable storage medium being inserted in the slide-in-module of the first analysis device or connected to the first analysis device during a startup of the first analysis device, wherein if the removable storage medium is not available, then operation of the first analysis device is not permitted at all.

9. The process according to claim 8, wherein the removable storage medium comprises a hardware token which is necessary for the operation of the analysis device.

10. The process according to claim 8, wherein the process further comprises checking an available removable storage medium for whether a data stock present on the removable storage medium originates from a different analysis device and, if this applies, importing the redundantly stored data contained in the removable storage medium into the internal memory medium of the analysis device.

11. The process according to claim 10, wherein the decision whether data redundantly stored in the removable storage medium are imported into the analysis device is dependent on a user interaction.

12. The process according to claim 10, wherein the import of data redundantly stored on the removable storage medium is recorded, in particular in an audit trail.

13. An analysis device for the management of data for carrying out the process according to claim 1, comprising
   an internal memory medium for storing newly created or modified data; and
   a memory interface for accessing a non-volatile removable storage medium so that, with the aid of the memory interface, the newly created or modified data can be continuously and automatically stored in a redundant manner in the removable storage medium during the body fluid analysis operations of the analysis device;
   wherein the analysis device is a medical/diagnostic analysis device configured to receive as input and analyze body fluids.

14. The analysis device according to claim 13, wherein the body fluid is blood.

15. A system comprising two analysis devices according to claim 13, wherein data which are continuously newly created or modified in one of the two analysis devices during the operation of one analysis device and data redundantly stored in the removable storage medium serve for the operation of the other analysis device, if the other analysis device accesses the removable storage medium.

16. A computer program product which is loadable directly into a main memory of a programmable analysis device and comprises program code sections which implement the process according to claim 1 if the computer program product is executed by means of the analysis device.

17. The process according to claim 1, wherein the process further comprises directly inserting the non-volatile removable storage medium in a slide-in-module of the first analysis device.

18. The process according to claim 17, wherein the act of physically transferring comprises providing the non-volatile removable storage medium from the first analysis device to a slide-in-module of the second analysis device.

19. The process according to claim 17, wherein the act of physically transferring comprises providing the non-volatile removable storage medium from the slide-in-module of the first analysis device to a slide-in-module of the second analysis device.

20. The process according to claim 1, wherein the process further comprises checking the availability of the removable storage medium being inserted in the slide-in-module of the first analysis device or connected to the first analysis device during a startup of the first analysis device, wherein if the removable storage medium is not available, then operation of the first analysis device is permitted to a limited extent, but without redundantly storing the data on the removable storage medium.

21. An analysis system comprising:
   a pair of equivalent medical/diagnostic devices configured to receive as input and analyze body fluids, each medical/diagnostic device has an internal memory medium and a non-volatile removable storage medium, and each medical/diagnostic device is configured to:
      newly create or modify data in the internal memory medium, and continuously and automatically store the newly created or modified data in a redundant manner in the non-volatile removable storage medium as at least body fluid analysis operations are conducted by the medical/diagnostic device and without synchronization of data stored in the internal memory medium of the medical/diagnostic device;
      import the data redundantly stored on the non-volatile removable storage medium of the other medical/diagnostic device into internal memory medium upon insertion of the non-volatile removable storage medium into a slide-in-module of the first analysis device or connection of the non-volatile removable storage medium to the first analysis device by a physical transfer of the non-volatile removable storage medium between the first and second analysis devices; and subsequent to the physical transfer of the non-volatile removable storage medium between the first and second analysis devices, both configure automatically the second analysis device to have the identical configuration to the first analysis device based on the imported data via a startup process and continue automatically with the body fluid analysis operations previously conducted by the other medical/diagnostic device based on the imported data, said imported data being at least configuration data which represents device settings that comprise language, IP address, display screen, country settings, energy management, network settings, calculated and displayed measuring units, measuring parameters used, measuring, calibration and quality control limits, quality measurement materials, security settings, audio settings, and/or planned automatic executions of analyzer functions and/or peripheral devices.

\* \* \* \* \*